United States Patent [19]

McDaniel

[11] Plant 4,082

[45] July 26, 1977

[54] ROSE PLANT-MELISSA VARIETY

[75] Inventor: Gayle Kent McDaniel, Carlton, Oreg.

[73] Assignee: Carlton Rose Nurseries, Carlton, Oreg.

[21] Appl. No.: 689,641

[22] Filed: May 24, 1976

[51] Int. Cl.[2] ..... A01H 5/00

[52] U.S. Cl. ..... Plt./18

[58] Field of Search ..... Plt./18–19

*Primary Examiner*—Robert E. Bagwill

*Attorney, Agent, or Firm*—Burns, Doane, Swecker & Mathis

[57] ABSTRACT

A rose plant of the Hybrid Tea Class obtained as a seedling from seed parent No. 1968-L and pollen parent No. 167-D. The rose plant of the new and distinct variety abundantly yields long lasting medium-sized blooms on a continuous basis in a greenhouse.

17 Drawing Figures

SUMMARY OF THE INVENTION

The object of the present invention is to provide a rose-plant of the Hybrid Tea Class which is capable of yielding an abundant quantity of quality cut flowers under greenhouse conditions.

The variety of rose-plant of the present invention was obtained at Hillsboro, Ore., as a seedling from seed parent No. 1968-L and pollen parent No. 167-D. The crossing was made during April, 1970, sowing during March, 1971, and the first flower appeared during July, 1971.

Asexual reproduction of my new and distinct variety shows that its unique combination of characteristics come true to form and are established and transmitted through succeeding propagations.

BRIEF DESCRIPTION OF THE DRAWINGS

The accompanying photographs show typical specimens of the vegetative growth and flowers of the new variety in different stages of development and are depicted in color as nearly true as it is reasonably possible to make the same in color illustrations of this character:

FIG. 3 shows the bud of the flower;

FIG. 4 shows the flower when starting to open;

FIG. 5 shows the flower when completely opened;

FIG. 6 shows the outer petal, top-inside surface, bottom-outer surface;

FIG. 7 shows intermediate petal, top-inside surface, bottom-outer surface;

FIG. 8 shows inner petal, top-inside surface, bottom-outer surface;

FIG. 9 shows a receptacle with the stamens showing;

FIG. 10 shows a receptacle showing the pistils after removing the stamens;

FIG. 11 shows a developing hip;

FIG. 12 shows one of the leaves with a composition of five leaflets showing the upper surface;

FIG. 13 shows one of the leaves with a composition of five leaflets showing the under surface;

FIG. 14 shows two of the young leaves, upper surface on one composed of three leaflets and the under surface of one composed of five leaflets;

FIG. 15 shows a portion of main stem and branching;

FIG. 16 shows branches; and

FIG. 17 shows two new growths, one with a developing bud.

DETAILED DESCRIPTION OF THE DISCLOSURE

Figure 1:
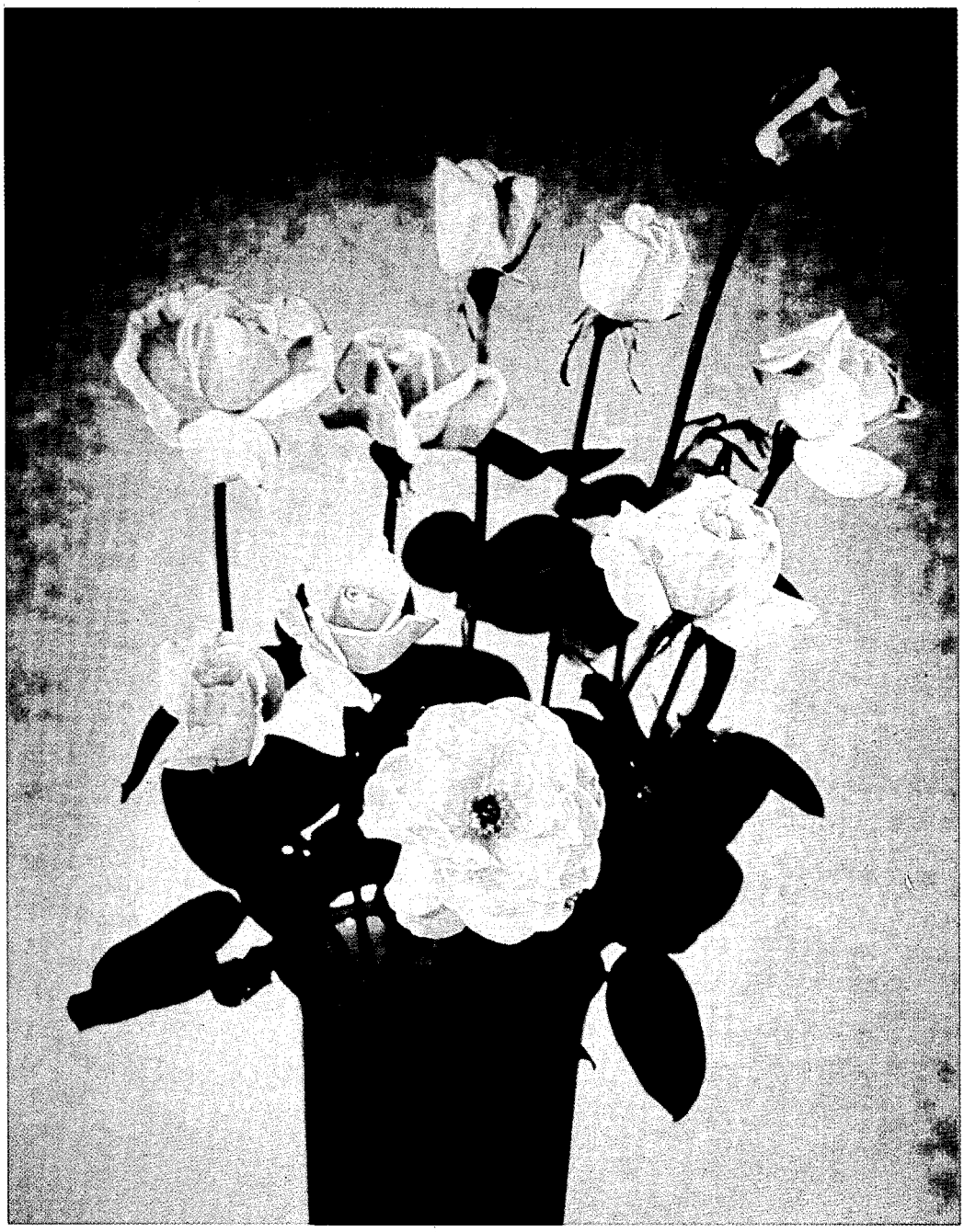
FIG. 1 is a view of the flower in different stages of development.
Figure 2:
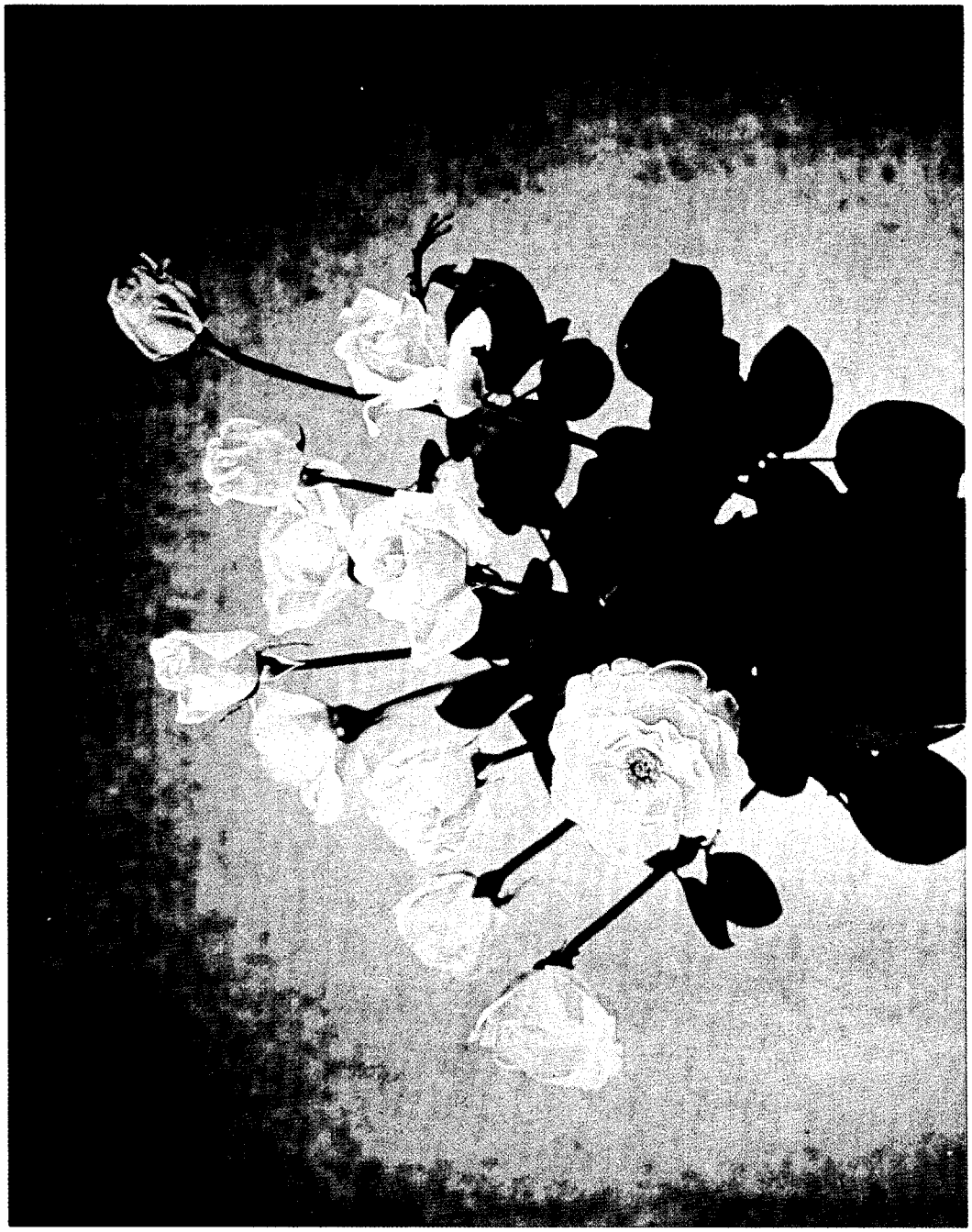
FIG. 2 is an additional view of the flower in different stages of development.

The following description was made of rose-plants of the new and distinct variety growing in a greenhouse at Watsonville, Calif. Color designations are to *A Dictionary of Color* by A. Maerz and M. Rea Paul, and in some instances where specifically indicated to the *Wilson Colour Chart,* I and II.

FLOWER:

Flowers borne: singly to stems; on normal, medium stems.

Quantity of bloom: abundant in greenhouse.

Continuity: continuous.

Fragrance: slight; tea.

Bud:

*Peduncle.*—Medium; erect; stiff; light green; entirely smooth; few prickles; yellow green.

*Before calyx breaks.*—Size: medium. Form: medium; pointed with a conspicuous neck; with foliaceous appendages on the surface of the bud; with medium, bristle-like foliaceous parts extending beyond the tip of the bud equal to $\frac{1}{4}$–$\frac{1}{2}$ or more of its length.

*As calyx breaks.*—Color: Plate 3B, 9 Rose Dawn.

*As first petal opens.*—Form: medium ovoid. Color: Outside: Plate 3K, 1 Eugenia Red. Inside: Plate 3I, 3 Weigela. Opening: It does open up well.

Bloom:

*Size when fully open.*—Medium: $3\frac{1}{4}''$ to $4''$.

*Petalage.*—Double (but stamens not hidden); from 27 to 32 petals; arranged regularly.

*Form.*—Open high at first; becoming flat open; globular; petals remaining at first loosely cupped inward; becoming later at maturity very loosely rolled outward.

Petals: medium leathery; with inside velvety; outside satiny.

*Shape.*—Outer: ovate; scalloped with base flat; with 2 notches. Intermediate: ovate undulate; with 1 tooth; with 2 notches. Inner: ovate; scalloped irregular; with 2 notches.

*Color.*—Colors may be modified by being shaded with other shades of pink.

*Color of a newly opened flower.*—Outer petal: Outside surface: Wilson: Camellia Rose $622_2$. Inside surface: Wilson: Camellia Rose $622_3$. Intermediate petal: Outside surface: Wilson: Spinel Pink $0625_3$. Inside surface: Wilson: Dawn Pink $523_1$. Inner petal: Outside surface: Wilson: Camellia Rose $622_1$. Inside surface: Wilson: Dawn Pink 523.

*Color of flower 3 days after opening.*—Outer petal: Outside surface: Wilson: Rhodamine Pink 527. Inside surface: Wilson: near Camellia Rose $622_1$. Inner petal: Outside surface: Wilson: Camellia Rose 622. Inside surface: Wilson: Camellia Rose $622_1$. Behavior: drop off cleanly; fading brownish-light pink. Flower longevity: cut roses grown in greenhouse kept at living room temperatures 6–9 days in December.

REPRODUCTIVE ORGANS

Stamens: very many; arranged regularly about pistils mixed with an occasional petaloid.

Filaments: many; most with anthers; medium.

*Color.*—Plate 3H, 5 Spinel Red.

Anthers: all open at once.

*Color.*—Plate 9, 1, 7 Deep Chrome. Seldom fused with a petaloid.

Pollen: very abundant; gold.

Pistils: many.

Styles: uneven; medium; thin; very loosely bunched.

Stigma: yellow.

Ovaries: all enclosed in receptacle.

Hips: medium ovoid with inconspicuous neck; pear-shaped; smooth walls; thick; fleshy; green.

Sepals: permanent; long; spear-shaped; recurved.

Seeds: few; medium large.

PLANT

Foliage:

*Leaves.*—Compound of 3 and 5; normal; medium; leathery; wrinkled.

*Leaflet.*—Shape: ovoid; with apex obtuse; base round; margin simply serrate.

*Color.*—Mature upper surface: Plate 23 J, 8 Mt. Vernon Green. Under surface: Plate 22 B, 6 Palmento. Young upper surface: Plate 22, 1, 6 Peridot. Under surface: Plate 23 L, 3 Hellebore Green.

Rachis (the supporting stem of the compound leaf): medium.

*Upper side.*—Smooth.

*Under side.*—Smooth.

Stipules: long; medium width; with long points; turning out at an angle of less than 45°.

Disease: resistant to mildew, blackspot. Resistance comparable to the average variety growing under the same cultural conditions.

GROWTH

Habit: bushy; upright; much branched.

Growth: very vigorous.

Canes: medium.

Main stems: bright.

*Color.*—Plate 22 K, 7 Spinach Green.

*Prickles.*—Many. Color: Plate 15 E, 10 Olive Wood.

*Hairs.*—None.

Branches: bright.

*Color.*—Plate 22 H, 7 Garland Green.

*Prickles.*—Several. Color: Plate 13 J, 9 Hazel. Hairs: none.

New Shoots: bright.

*Color.*—Plate 15 C, 9 Teakwood, underside of new leaves reddish-purple.

*Prickles.*—Several. Color: Plate 4 K, 9 Doge at base: Plate 15 E, 8 Mustang at tip. Hairs: none.

Having thus described and illustrated my new variety of rose plant what is claimed as new and desired to be secured by Letters Patent is:

1. A new and distinct variety of rose plant of the Hybrid Tea Class obtained as a seedling from seed parent No. 1968-L and pollen parent No. 167-D characterized by its ability to yield medium-sized long lasting blooms on a continuous basis in a greenhouse substantially as shown as described.

* * * * *

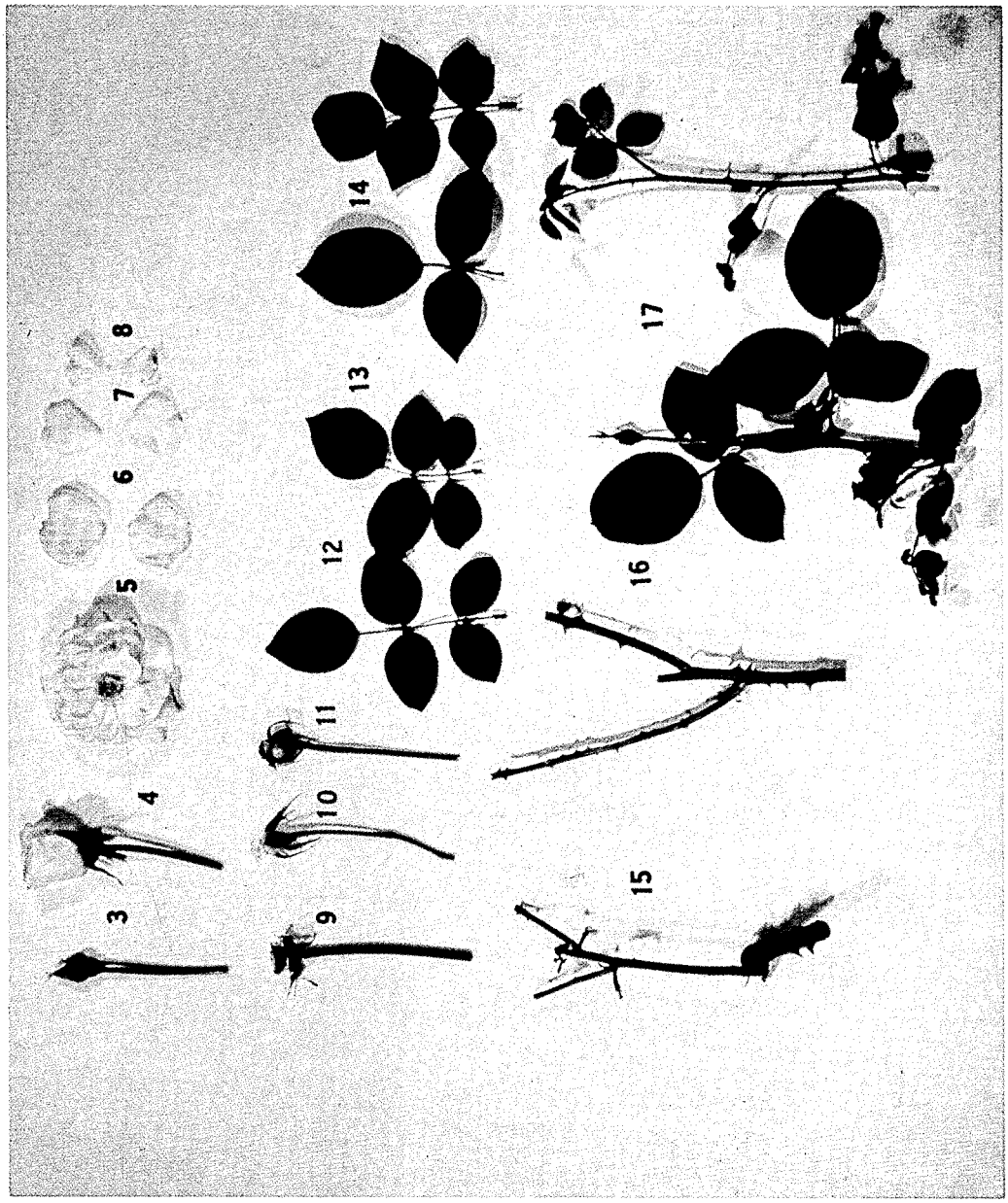
3
4
5
6
7
8
9
10
11
12
13
14
15
16
17